(12) United States Patent
Arabani et al.

(10) Patent No.: US 10,383,314 B2
(45) Date of Patent: Aug. 20, 2019

(54) EMPATHY MONITORING AND DETECTION SYSTEM

(71) Applicant: Autodesk, Inc., San Rafael, CA (US)

(72) Inventors: Negar Arabani, Mill Valley, CA (US); Mark Thomas Davis, Mill Valley, CA (US); James Awe, Santa Rosa, CA (US); Patricia Anne Vrobel, Portland, OR (US); Douglas Look, San Francisco, CA (US)

(73) Assignee: Autodesk, Inc., San Rafael, CA (US)

( * ) Notice: Subject to any disclaimer, the term of this patent is extended or adjusted under 35 U.S.C. 154(b) by 414 days.

(21) Appl. No.: 15/212,039

(22) Filed: Jul. 15, 2016

(65) Prior Publication Data

US 2018/0014512 A1    Jan. 18, 2018

(51) Int. Cl.
| A62B 35/00 | (2006.01) |
| A01K 29/00 | (2006.01) |
| A01K 27/00 | (2006.01) |
| A01K 11/00 | (2006.01) |
| H04N 7/18 | (2006.01) |
| A61B 5/11 | (2006.01) |
| A61B 5/00 | (2006.01) |
| A61B 5/0205 | (2006.01) |
| A61B 5/024 | (2006.01) |
| A61B 5/08 | (2006.01) |

(52) U.S. Cl.
CPC .......... *A01K 29/005* (2013.01); *A01K 11/008* (2013.01); *A01K 27/001* (2013.01); *A01K 27/009* (2013.01); *A61B 5/1113* (2013.01); *A61B 5/6805* (2013.01); *H04N 7/185* (2013.01); *A61B 5/02055* (2013.01); *A61B 5/02438* (2013.01); *A61B 5/0816* (2013.01); *A61B 5/1117* (2013.01); *A61B 2503/40* (2013.01); *A61B 2560/0214* (2013.01); *A61B 2560/0242* (2013.01)

(58) Field of Classification Search
None
See application file for complete search history.

(56) References Cited

U.S. PATENT DOCUMENTS

2007/0095304 A1* 5/2007 Rosenberg ........... A01K 11/008
                                                    119/720
2016/0029962 A1* 2/2016 Hyde ..................... A61B 5/117
                                                    600/301

(Continued)

*Primary Examiner* — Richard G Davis
(74) *Attorney, Agent, or Firm* — Fish & Richardson P.C.

(57) ABSTRACT

A method includes providing a wearable device compatible with and worn by an animal, the wearable device including a processing engine, a plurality of sensors, and a communication interface to a remotely located base station. The method includes monitoring an environment around the wearable device as the animal traverses a space and collecting information based on data generated by the plurality of sensors. The method also includes analyzing the data generated by the plurality of sensors and inferring activities associated with a human in proximity to the animal, wherein inferring activities includes determining a current location of the human based on data generated by one or more of the sensors, and determining activities of the human over a period of time based on data generated by the one or more sensors.

16 Claims, 6 Drawing Sheets

(56) References Cited

U.S. PATENT DOCUMENTS

| | | | |
|---|---|---|---|
| 2016/0029963 A1* | 2/2016 | Hyde | A61B 5/1171 600/301 |
| 2016/0302392 A1* | 10/2016 | Pantazes | A01K 29/005 |
| 2017/0318789 A1* | 11/2017 | Pantazes | A01K 15/021 |
| 2018/0235182 A1* | 8/2018 | Bocknek | A01K 29/005 |

* cited by examiner

EMPATHY MONITORING AND DETECTION SYSTEM

BACKGROUND

This specification relates to a monitoring and detection system used to monitor patients and residents in a residence or a facility such as health care facility and long term or short term care facilities. A portion of the monitoring and detection system may be worn by an animal, such as a dog.

Researchers conducting studies have hypothesized that domestic dogs are able to share empathic-like responses towards humans, even if the human subject is someone unfamiliar to the dog. One such study involved researchers observing the behavior of individual dogs interacting with their owner and a stranger as participants, all within an enclosed area. During a first part of the study the owner and stranger engaged in various activity including talking and humming. In response, the individual dog did not show any change in behavior. During a second part of the study, one of the owner or stranger would pretend to cry and/or show signs of distress. In response, the individual dog directed their behavior toward the participant showing signs of distress, regardless of whether the participant showing signs of distress was the owner or the stranger. The participant that was crying or showing signs of distress was approached by the dog in a submissive fashion, and exhibited behavior including sniffing, licking and nuzzling the distressed participant. The researchers noted that the dogs being observed did not exhibit typical forms of excitement including tail wagging or panting toward the participants. It was hypothesized that because the dogs did not direct their behavior responses showing empathy solely toward their owner, that the dogs were seeking out human participants showing signs of distress. This research may show that dogs have the cognitive capacity for empathy, and the ability to direct empathy toward humans.

The use of video cameras to monitor patients in a care facility may be necessary but does not generally provide a compassionate or empathetic experience for the patient. While a personal visit from a healthcare professional can provide an empathetic experience for a patient, the patient may receive additional benefits when visited by an animal, such as a dog, where the animal is also capable of monitoring the environment around the patient, especially if the dog is able to express empathetic behavior toward the patient. What is needed is a more empathetic way to monitor patients that are receiving monitored care in a facility such as in a private residence, a nursing home, short term care facility, and/or long-term care facility, that moves away from the use of video cameras that are monitored from a central location.

SUMMARY

An innovative aspect of the subject matter described in this specification may be implemented in a method that includes providing a wearable device compatible with and worn by an animal, the wearable device including a processing engine, a plurality of sensors, and a communication interface to a remotely located base station. The method includes monitoring an environment around the wearable device as the animal traverses a space and collecting information based on data generated by the plurality of sensors. The method also includes analyzing the data generated by the plurality of sensors and inferring activities associated with a human in proximity to the animal, wherein inferring activities includes determining a current location of the human based on data generated by one or more of the sensors, and determining activities of the human over a period of time based on data generated by the one or more sensors. The method also includes reporting the activities associated with the human to a central service; evaluating the reported activities; and providing information to an entity associated with the human related to the activities or the environment of the human.

These and other implementations can each optionally include one or more of the following features. The method may further include tracking an amount of movement of the animal over a period of time. The method may further include tracking where and how often the animal moved to a specific location. Determining activities of the human over a period of time may further include evaluating the activities to detect whether the human is in danger. Determining activities of the human over a period of time may further include evaluating the activities to detect whether the human is following prescribed procedures. As part of the method, the animal may be one of a dog, a cat, and a horse. The animal may be a dog that is trained to stay in close proximity to the human.

Activity information of the human over a period of time may be recorded in a data storage and compared to historical activity information of the human to determine an activity level. The method may further include recording, in a data storage, activity information of the human over a period time, and comparing the activity information to historical activity information of the human to determine an activity level. The method may further include determining whether the determined activity level exceeds a predetermined minimum activity level for the human. The method may further include providing the wearable device with a communication interface to enable the central service to command the animal to go to a certain location.

Another innovative aspect of the subject matter described in this specification may be implemented in a monitoring and detection system that includes a wearable device compatible with and worn by an animal, the wearable device including a processing engine, one or more input/output devices, and a communication interface to communicate with a remotely located base station. A sensor array is integrated within the wearable device, the sensor array including a plurality of sensors configured to monitor an environment around the wearable device as the animal traverses a space that is proximate to a human, and generate data representing attributes of the environment and activities of the human. A camera is mounted to the wearable device, the camera being positioned for capturing images within a field of view of the animal as the animal traverses the space and observes the human.

These and other implementations can each optionally include one or more of the following features. The system may include an observation module worn by the animal for detecting engagement of the animal with the human. The observation module may include a sensor for detecting motion of the animal, and one or more sensors for detecting physiological parameters of the animal. The one or more sensors for detecting physiological parameters of the animal may further include one or more of a heart rate monitor for detecting a heart rate of the animal, a respiration monitor for detecting respiration of the animal, or a temperature sensor for detecting a body temperature of the animal. The observation module may collect sensor data from the sensors and transmit the sensor data to the processor engine using wireless communication. The processing engine may store and further process the sensor data to determine a likelihood that the animal is expressing empathy toward the human. The camera may be one of a still camera or a video camera.

Particular implementations may realize none, one or more of the following advantages. An animal such as a dog, monitoring a person requiring care or assistance with their daily routine, can provide companionship for the person being monitored. Additionally, monitoring the person without the use of cameras in their room or living space provides a less intrusive and more compassionate way to monitor the person's wellbeing. The dog that is providing companionship also may behave in an empathetic and caring way toward the person being monitored. For example, the dog may recognize that the person being monitored has limited mobility and can move closer to the person or nuzzle them so that the person can pet and interact with the dog. The companionship, interaction and empathetic behavior of the animal may serve to improve the overall emotional wellbeing of the person being monitored. The dog also may have the ability to sense when the person being monitored is particularly distressed, and if adequately trained, can bark or otherwise signal through the monitoring and detection system within the vest and alert a supervisor attending the base station server that additional assistance is needed. If the supervisor monitoring the base station server is watching live video/audio from the camera/microphone mounted to the vest, the supervisor may notice that the person being monitored requires additional assistance. At that point the supervisor can decide whether to speak with the person through the communication link in the vest, issue a command to the animal (e.g., the dog), or request that an assistant personally visit and attend to the person being monitored. As an additional benefit, information and data collected by the sensor on the vest can be further processed and used for other purposes (e.g., tracking, analysis, pattern recognition in the data, or for generation of feedback). Other uses of the monitoring and detection system are possible.

The details of one or more implementations of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Systems, methods, devices and computer program products are described for implementing a monitoring and detection system used to monitor patients and/or residents in a residential setting or a facility such as assisted living facilities, retirement facilities, health care facilities and long term or short term care facilities.

Figure 1:
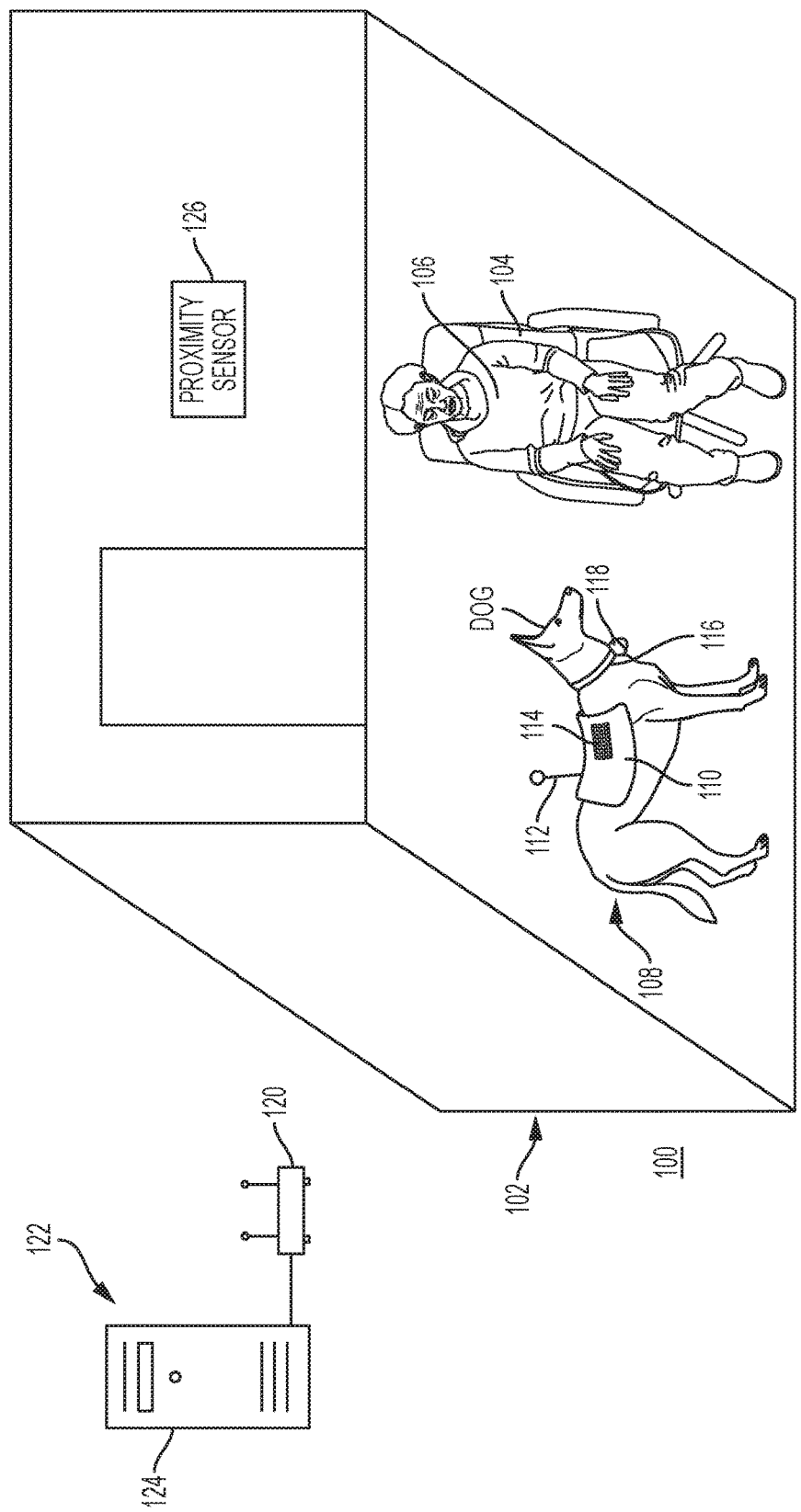
FIG. 1 is a diagram of an example environment for operating a monitoring and detection system.

FIG. 1 shows an example environment for operating the monitoring and detection system 100 of the present disclosure. In the implementation shown, a setting (e.g., residential or facility) includes one or more rooms 102. Each room 102 allows space for providing living (assisted or otherwise), nursing care, or rehabilitation services for the residents. The room 102 may for example include a chair 104, and other furniture such as tables, couches and/or beds, not specifically shown. The room 102 or several rooms may define living space or care space for a person 106 being monitored. The exemplary environment shows an animal, such as a dog 108 that is appropriately trained and tasked with interacting with and also monitoring the person 106. The dog 108 is shown wearing a vest 110 with associated electronics that forms one portion of the monitoring and detection system 100. In alternate implementations the animal could be a cat or other animal and the electronics associated with the vest 110 could be integrated into a smaller module worn on a collar. As will be described in greater detail, the vest 110 includes various electronic components that assist with monitoring the person 106, collecting data associated with the person 106 and their surrounding environment, and communicating the collected and/or further processed data through a bi-directional wireless communication link 120 (e.g. a Wi-Fi® enabled router) with a base station 122 having (or being associated with) at least one server 124. In some implementations the server 124 may be networked with other computers or other servers. In some implementations the server 124 may be a cloud based server that communicates with the wireless communication link 120 and receives data collected by the vest 110. In the example implementation shown, the room 102 is also shown to include a proximity sensor 126 that may be configured to operate in multiple ways when the presence of an animal or person is detected. For example, the proximity sensor 126 may be configured to turn a light on when the dog or person enters the room, or control other elements (e.g., heat, window shades, music, or activate other sensors) in the room.

In some implementations, the server 124 is a local server for the residence or facility and the local server sends information about the person being monitored to a central service. For example the central service may include a server or group of servers and data storage (not shown) that collects information from multiple residences/facilities and provides secure access to information about the patients or residents being monitored at the residences/facilities to specific people with a need to access such information (e.g. doctors treating the patient, family members, spouses, and parents of children). In some implementations the server and data storage for the central service may be a cloud based system.

In some implementations, the vest 110 includes a suitable antenna 112 for communicating with the wireless communication link 120 of the base station 122. The antenna 112 is generally depicted in schematic form for purposes of illustration, but in practice the antenna 112 can be integrated into the body of the vest 110 as a low power antenna that is generally not visible. In some implementations, the vest 110 also includes a video camera 114 that is capable of capturing still images, video and audio as the animal (dog) moves throughout the room 102 and facility. The video and audio signal may be recorded on a memory within the video camera 114 and additionally or alternatively streamed from the electronics within the vest 110 back to the base station 122 and recorded and displayed on a monitor. The dog 108 is also depicted wearing a collar 116 that positions an empathy observation module 118 around the dog's neck. The components and features of the empathy observation module 118 are described in greater detail below.

Figure 2:
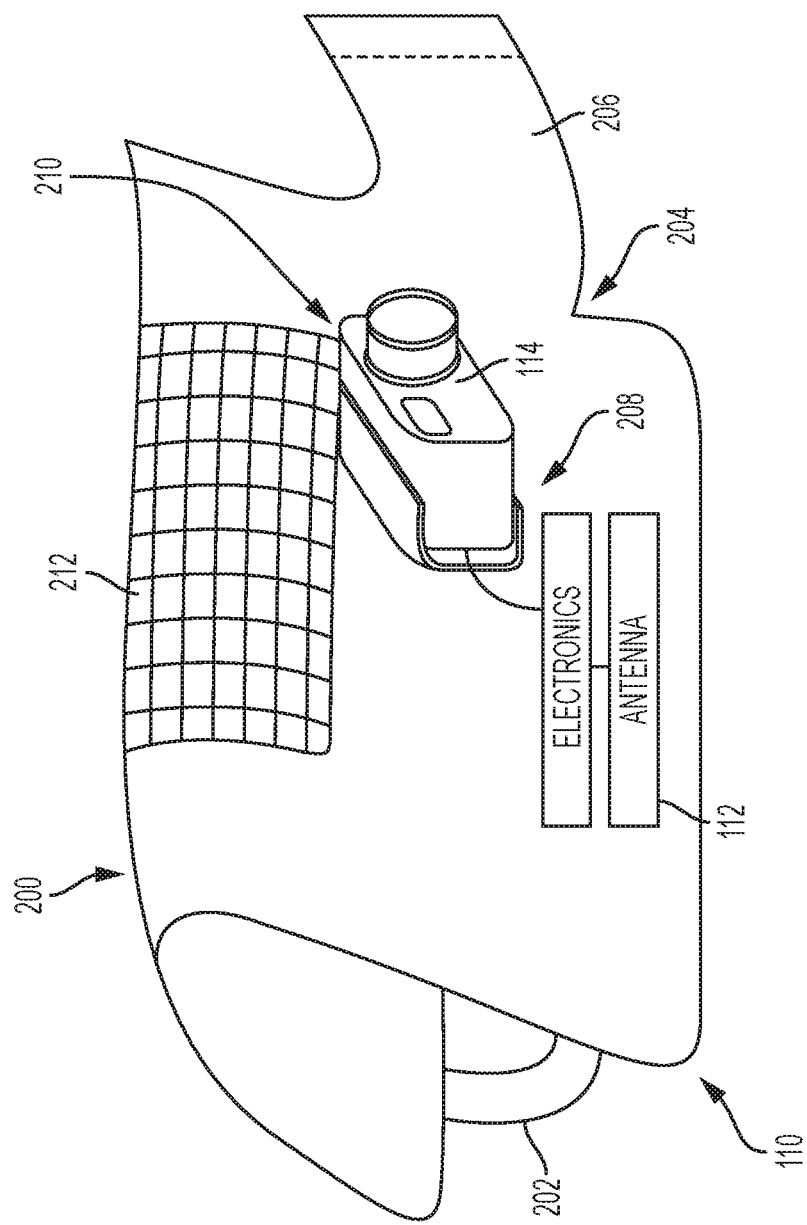
FIG. 2 is a diagram of a vest worn by a service or working animal that contains the monitoring and detection system.

FIG. 2 shows a diagram of the vest 110 depicted in FIG. 1. The dog 108 may be a trained service animal or may be trained for other purposes such as assisting the facility with monitoring of a person or patient while also providing empathy toward the person. In some implementations the dog may be trained to stay in close proximity to the person so that the person is within the field of view of the video camera 114 and the sensors within the vest can adequately collect and generate data about the person and the person's environment. While the vest 110 and monitoring and detection system 100 is described as being used with an animal such as a dog, it should be understood that the vest 110 and monitoring and detection system 100 is not limited to being used with dogs can be used with other animals (e.g., cats, horses, goats, or other domesticated animals).

The vest 110 is preferably a fabric body structure 200 that drapes over the length of the back of the animal and extends down and around the sides of the animal. Straps 202 which may include hook and loop material fasteners attached to the body structure 200 are used to secure the vest to the animal so that the vest is both comfortable and is prevented from moving from its intended position. The body structure 200 also may be designed to include holes 204 for accommodating the front legs of the animal, and may include a front fabric portion 206 that wraps around the animal's chest. In some implementations the empathy observation module 118 may be integrated into the front fabric portion 206 as opposed to being secured by a separate collar 116. In some implementations, a variety of pockets and compartments are formed in the body structure 200 of the vest to contain and secure the components, sensors and electronics 208 of the monitoring and detection system 100. In some implementations, a forward portion of the vest 110 includes a camera mounting post 210 that allows video camera 114 to be securely attached to the body structure 200. The mounting post 210 allows the video camera 114 to be properly aligned and aimed so that as the animal moves about performing its assigned tasks, the video camera 114 will see the appropriate field of view for capturing images of generally what is seen by the animal as it moves (for example through a building, facility or other setting). The video camera 114 may capture and store still or preferably video images on a memory card within the camera, or may transmit live video back to a base station via other electronic components 208 associated with the monitoring and detection system 100.

The body structure 200 can also be designed to include suitable compartments for containing a power supply such as a rechargeable battery. In some implementations the body structure 200 may include a flexible solar panel 212 secured along the top portion thereof that is operable to provide electricity to the electronics 208 and recharge the power supply when suitable sunlight is available. Such an implementation is particularly useful when the animal is a working dog on a farm or ranch and may be outdoors for extended periods of time or away from a separate charging source.

Figure 3:
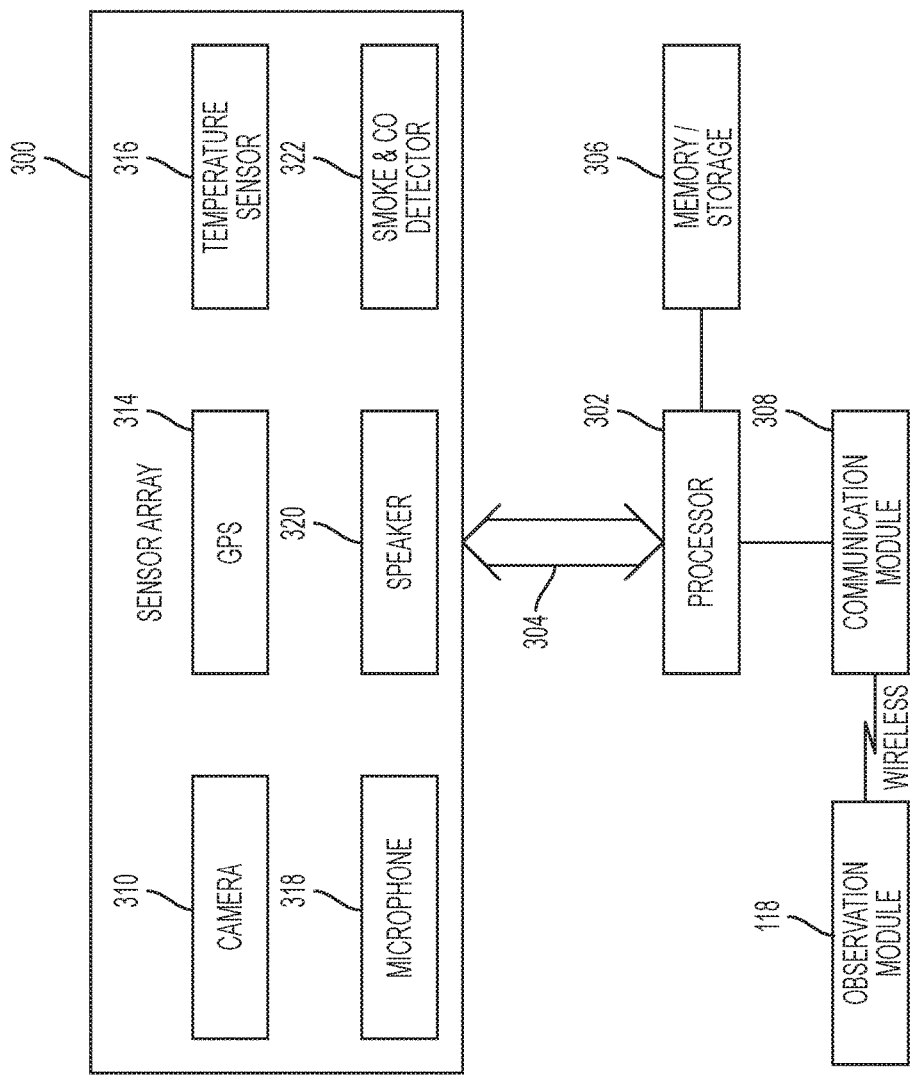
FIG. 3 is a block diagram of the various components and sensors forming the monitoring and detection system.

FIG. 3 shows a block diagram of the components and sensors of the electronics 208 that form part of the monitoring and detection system 100. The electronics 208 include a sensor array 300 that communicates with a processor 302 through a communication link or bus 304. The processor 302 is also connected to a suitable memory and data storage 306. In some implementations the bus 304 is a USB enabled communications bus that allows the processor 302 and memory 306 to communicate with the various components and sensors in the sensor array 300. The processor 302 is also connected to a communication module 308 to facilitate bi-directional communication with the base station 122. In some implementations, the communication module 308 includes electronics to communicate with a variety of wireless devices using a wide range of communication standards and protocols including Wi-Fi®, Bluetooth®, and GPRS, 3G, 4G, LTE, or any suitable data communication standard for communicating voice and/or data over a mobile telecommunications network. The communication module 308 may communicate with the base station 122 to allow data transfer between the vest electronics 208 and the base station server 124. The communication module 308 also may communicate with other suitably equipped vests 110 having appropriate communication electronics in a peer-to-peer or mesh network arrangement. Thus, in some implementations a plurality of animals wearing vests 110 can be networked so that data collected by the vests can be aggregated (e.g. which dogs have visited which persons), and after further analysis, decisions can be made about what future commands or tasks are issued to each animal.

The communication module 308 also communicates directly with the empathy observation module 118 using, for example, a wireless personal area network technique such as Bluetooth® technology which allows data collected by the sensors in the empathy observation module 118 to be stored in memory 306 and further processed and analyzed by processor 302. The data collected by the sensors in the empathy observation module 118 can also be communicated directly to the base station 122 through the communication module 308. As described above, the base station 122 is also configured to communicate information back to the vest electronics 208 and processor 302 through the communication module 308.

With continued reference to FIG. 3, in the implementation shown, the sensor array 300 includes a video camera 310 (the same video camera 114 shown in FIG. 1), a GPS module 314, an ambient temperature sensor 316, a microphone module 318, a speaker module 320, and optionally, a smoke and carbon monoxide detector module 322. In some implementations the various modules forming sensor array 300 are integrated into a small package that can be fitted into a suitably sized compartment formed in the side of the body structure 200 of the vest 110.

The GPS module 314 is used primarily for determining the location of the animal wearing the vest, either in a residence, facility, or on land if working outside. Data generated by the GPS module 314 can be used to track larger movements of the animal or dog over a period of time, and in some implementations may be used to track where and how often movement occurred to specific locations. The ambient temperature sensor 316 is used primarily for determining the temperature in the environment around the dog (such as the room 102) and around the person being monitored. The temperature sensor 316 is positioned such that it will not detect the body temperature of the dog and is thus a different temperature measurement from that taken by a separate temperature sensor associated with the empathy observation module 118.

The microphone module 318 is used as a sensor for monitoring specific sounds made by the dog during a time when the dog is observing or interacting with the patient or person being monitored. The microphone module 318 may also be used to monitor sounds made by the person being monitored (e.g. when they are asleep, experiencing pain, etc.), and may also allow the person being monitored to verbally communicate with another person back at the base station 122. The speaker module 320 allows a person at, for example, the base station 122 to verbally communicate with the person being monitored (e.g. a speaker phone associated with the vest), and also allows the person at the base station to issue commands directly to the animal. For example, a dog may be commanded to go to a specific location, or perform a specified task (e.g. in support of the monitoring functions of the system). In some implementations the sensor array 300 may include a smoke and carbon monoxide detector 322 to monitor the environment around the animal and the person being monitored.

Figure 4:
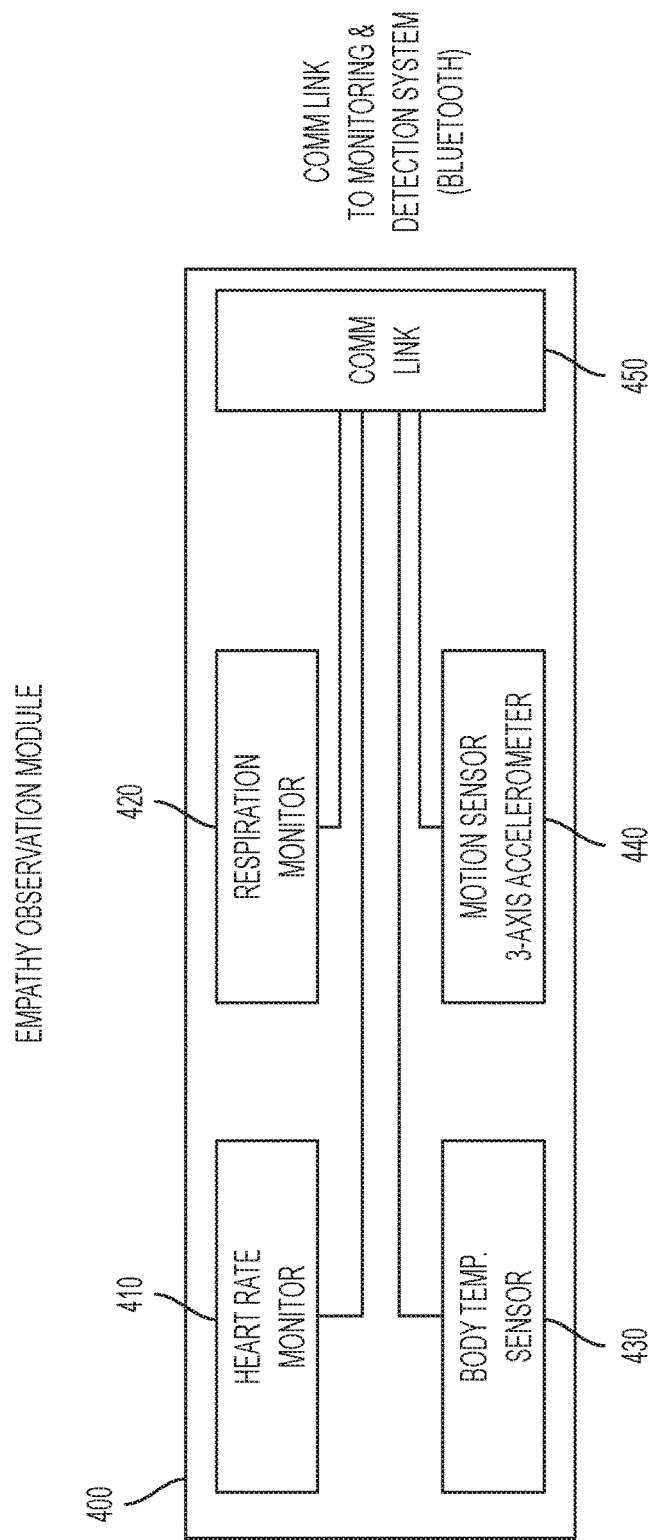
FIG. 4 is a block diagram of the various components and sensors forming the empathy observation module.

As introduced above, research with domestic dogs shows that dogs have the ability to express empathy toward humans, especially in situations where a human shows signs of distress. To better understand the potential for dogs to express empathetic behavior toward humans, the monitoring and detection system 100 includes an empathy observation module 400 (the same module 118 shown in FIG. 1) as one of the electronic components. FIG. 4 shows the various components and sensors that form the empathy observation module 400. The empathy observation module 400 is discussed with reference to a dog, but other animals may be fitted/may use the empathy observation module. A heart rate monitor 410 senses the heart rate of the dog so that changes in heart rate can be determined at a particular time and correlated with the activity of the dog and assist with determining empathetic behavior exhibited by the dog. A respiration monitor 420 senses the respiration or breathing pattern of the dog so that changes in breathing patterns can be determined at a particular time and correlated with the activity of the dog. For example when the dog engages a person being monitored, the heart rate monitor 410 can detect whether the dog's heart rate increases and the respiration monitor 420 can detect whether the dog's respiration increases. Further processing heart rate and respiration information for example with video information and even sound information may help understand and thus detect whether the dog is expressing empathetic behavior toward the person being monitored, as distinguished from an increase in heart rate because the dog is excited for example when the person being monitored is offering the dog a treat, or during exercise of the animal.

A temperature sensor 430 monitors the body temperature of the dog so that changes in body temperature can be tracked and correlated with the activity of the dog. In situations where the dog is working, for example, working outside on a farm or ranch, the temperature sensor 430 provides vital feedback about the body temperature of the dog so that the physical condition of the dog can be monitored. If the dog's body temperature is outside an acceptable range, this may indicate that a similar situation exists in the person being monitored. Detection of such a condition can result in the dog/and person being instructed to go inside or otherwise seek further assistance.

The empathy observation module 400 may also include a motion sensor 440 for detecting the motion, activity, intensity of the activity, and small movements of the dog toward the patient or person being monitored. The motion sensor 440 may include, for example, a three-axis accelerometer used to translate the general movement and intensity of the movement of the animal into digital measurements that are then further analyzed. In operation, the motion sensor 440 can determine whether the dog is moving very slowly or not moving at all in its behavioral response to the patient, and can determine whether the dog is actively engaging the patient and showing interest by for example sniffing or nuzzling the patient. Analysis of the accelerometer data in conjunction with GPS data and video data may allow the processor in the vest electronics 208 and/or the monitoring and detection system 100 to determine a likelihood that the dog is expressing empathy toward the patient or person being monitored. This detection can be important to determining whether the person being monitored is receiving what is intended to be empathetic behavior from the dog as part of a patient care plan. Further, evaluating of the combination of the motion sensor along with GPS data may allow for better position tracking, particularly in situations where data resolution is poor or GPS satellites are not visible.

The heart rate monitor 410, respiration monitor 420, temperature sensor 430, and motion sensor 440 communicate signals representing data collected by the various sensors to a communication link 450 that communicates this information to the vest electronics 208 and the monitoring and detection system 100 for further processing. In some implementations the communication link 450 communicates wirelessly with the communication module 308 using for example Bluetooth® technology. Data produced by the various sensors associated with the empathy observation module 400 is further analyzed by processor 302 associated with the monitoring and detection system 100, or a processor associated with the base station 122 to analyze and understand the behavior of the animal as well as to determine the likelihood of whether this behavior is an expression of empathy by the animal toward the patient or person being monitored.

In some implementations the components forming the empathy observation module 400 are integrated into a single electronic module (not specifically shown in FIG. 4) that can be attached to a collar worn by the animal. The electronic module may for example include a rechargeable battery as a power supply.

The empathy observation module 400 also includes a local processor and memory that can collect and process data about the activity of the dog in order to monitor the overall health of the dog, determine how active the dog has been during its tasks, how far it has walked, run, etc., and how much rest the animal receives. In a preferred implementation the empathy observation module 400 is a unique device that is assigned to and worn at all times by a specific dog so that activity level and overall health of that dog can be tracked separately from the activity level and overall health of other dogs or animals in the service group. When a dog is put into service and a vest 110 is attached to their body, the empathy observation module 400 can be paired with the vest electronics 208 using for example Bluetooth® technology. When the dog is taken out of service and the vest 110 is removed, the dog may retain the empathy observation module 400, for example, on their collar. Keeping the empathy observation module 400 separate from the vest electronics 208 allows a larger group of dogs to share a smaller number of vests 110 while retaining the ability to track the activity level and overall health of each animal on an ongoing basis.

Figure 5:
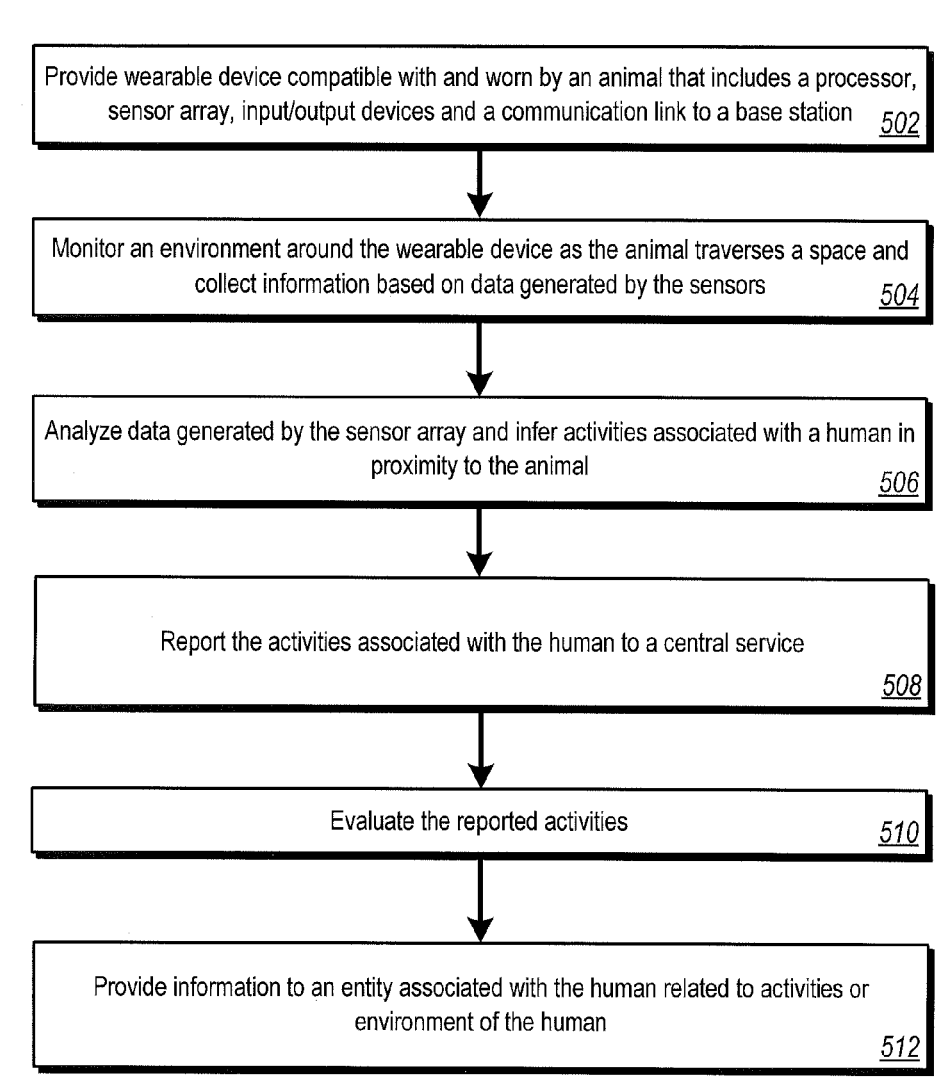
FIG. 5 is a flowchart of a an example process for using the monitoring and detection system

FIG. 5 is a flowchart of an example process 500 for using the monitoring and detection system 100 shown in FIGS. 1 to 4. In some implementations, the monitoring and detection system 100 can perform steps of the process 500 using instructions that are executed by one or more processors. FIGS. 1 to 4 are used to provide example structures and networked processor architectures for performing the steps of the process 500.

The animal, and in this exemplary implementation a dog 108, is fitted with a wearable device such as vest 110 that is compatible with the size of the animal (502). The vest 110 may include a variety of straps, hook and loop fastening material, buckles and/or webbing that allows the vest 110 to be comfortably secured to and/or around the body of the animal. In one implementation the vest 110 is outfitted with a set of electronic components that includes a processor or processing engine, for example processor 302; a plurality of sensors, for example sensor array 300; one or more input/output devices, for example video camera 114, microphone module 318, speaker 320, and optionally smoke and carbon monoxide detector 322; and a communications module 308 that provide bi-directional communication with a remotely located controller, such as base station 122.

Once the animal is fitted with the wearable device and the vest electronics 208 are communicating with the base station 122, the monitoring and detection system 100 monitors the environment around the wearable device as the animal traverses a space and collects information based on data generated by the sensor array 300 (504). As described above, the empathy observation module 400 also monitors various physiological attributes of the animal and the data generated by these sensors is communicated to the monitoring and detection system 100 for further processing. For example, if the dog is tasked with monitoring a person, the video camera 114 is able to stream video of the environment traversed by the dog and is able to capture video of the person being monitored so that this video can be reviewed either in real time by someone attending the base station 122, or stored for review at a later time.

In some implementations, the vest electronics 208 and temperature sensor 316 are able to determine the temperature in the environment of the person being monitored. If for example the temperature in the room 102 of the person being monitored is detected above or below a certain predetermined threshold, the monitoring and detection system 100 may send a signal to the base station 122 to automatically adjust a thermostat for the room 102. The microphone module 318 can be used to listen to words spoken by the person being monitored and/or sounds made by the animal, and the speaker module 320 can be used by someone attending the base station 122 to communicate directly with the person being monitored, and/or issue a command to the animal such as for example "sit for patient", "go to the next room", or "return to home". By viewing live video from the video camera 114, someone attending the base station 122 may determine that the person being monitored is asleep and may choose to command the dog to go to the next room or return to home.

Upon receiving data generated by the sensor array 300 and the empathy observation model 400, the monitoring and detection system 100 is able to monitor and infer activities associated with the person being monitored when proximate to the animal (506). The monitoring and inferring may include determining a current location of the person being monitored based on the data generated by the sensor array 300, and include determining various activities or an activity level of the person being monitored over a period of time based on data derived from one or more of the sensors in the sensor array 300. For example, optics and electronics within the video camera 114 may be operable to detect whether the person being monitored is asleep or is alert or awake based on detected subtle movements, and in conjunction with the processor 302, determine time periods for these activities when the animal is proximate to the person.

In some implementations the person being monitored can be fitted with a small activity monitor that includes a three-axis accelerometer (similar to motion sensor 440) that tracks characteristics that might include their motion, activity level (or lack thereof), intensity of their activity, and time spent either sedentary or sleeping. The activity monitor can collect and process this data and then transmit this data to the vest electronics 208 and thus to the monitoring and detection system 100 using for example a Bluetooth® wireless connection when the animal is proximate to the person being monitored.

Once a requisite amount of data is collected by the vest electronics 208 during the animal's engagement with the person being monitored, periodically or on command, the monitoring and detection system 100 can report the data representing the activities (and/or the activities themselves) of the person being monitored back to the base station 122 (508). The collected data can then be further analyzed and evaluated (510). In some implementations, information about the movement and/or activity level of the person can be compared to historical information about the person stored for example by server 124 to determine if the activity level of the person is insufficient or would otherwise set an alarm condition. In some implementations, the collected data can be used to track and/or evaluate and respond to indications or a determination that the person may be in danger, or is not following prescribed defined procedures.

The process 500 also allows the monitoring and detection system 100 and server 124 to provide information to an entity (e.g. physician, family member, care facility administration) associated with the person being monitored (512) that includes for example a report of the activities and activity level of the person, information about the person's living environment, trend analysis of the person's activity level, and other information that might be useful to the entity. For example, the person's primary care physician may be able to better understand whether the health and wellbeing of the person being monitored is improving or declining over time. Family members of the person being monitored may be able to have reassurance that the person is being well attended to, both by the staff of the care facility and potentially by the animal that is engaging with the person.

Figure 6:
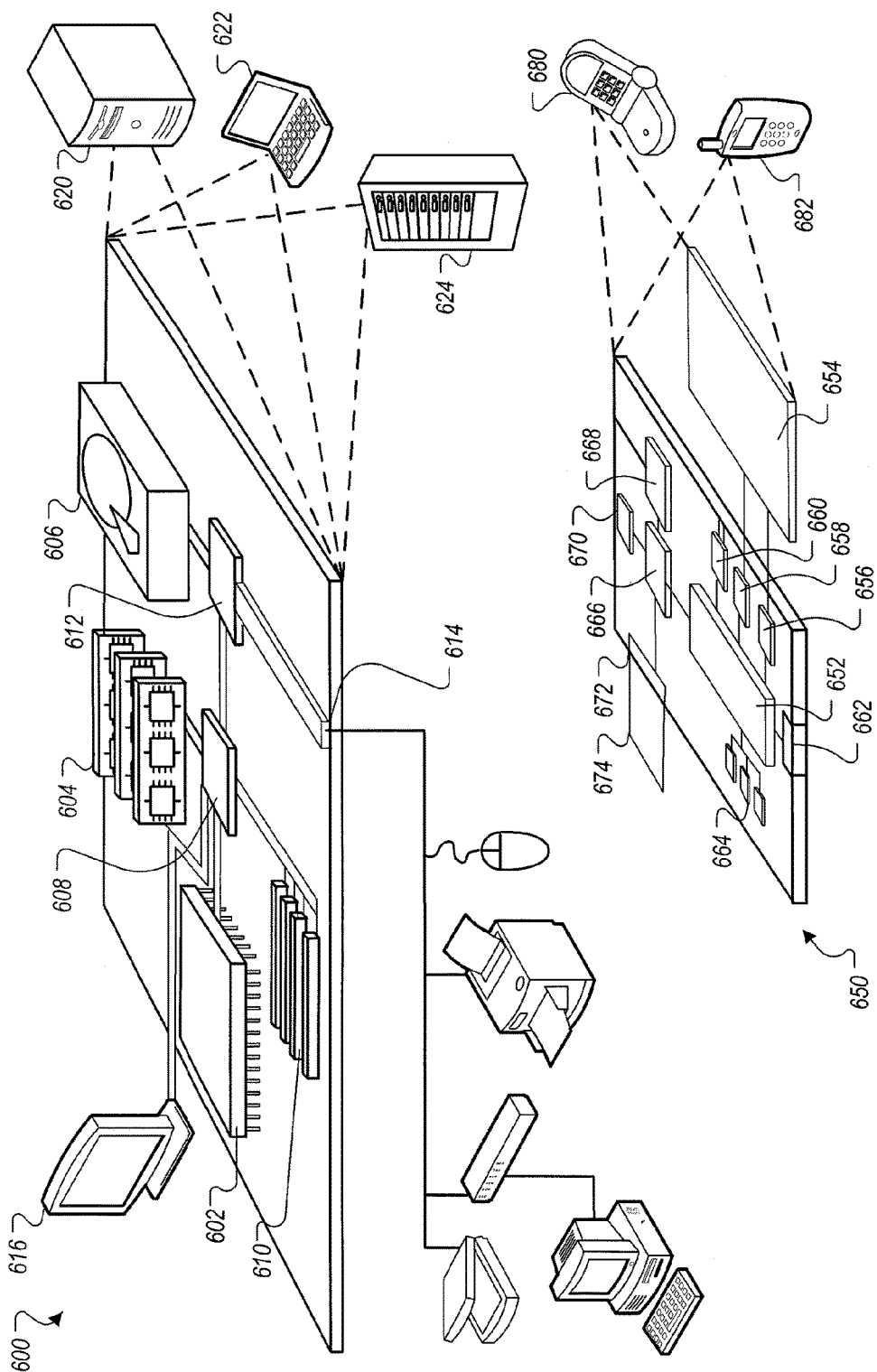
FIG. 6 is a block diagram of an example computer system that can be used to implement the methods, systems and processes described in this disclosure.

FIG. 6 is a block diagram of example computing devices 600, 650 that may be used to implement the systems and methods described in this document, as either a client or as a server or plurality of servers. Computing device 600 is intended to represent various forms of digital computers, such as laptops, desktops, workstations, personal digital assistants, servers, blade servers, mainframes, and other appropriate computers. Computing device 600 is further intended to represent any other typically non-mobile devices, such as televisions or other electronic devices with one or more processors embedded therein or attached thereto. Computing device 650 is intended to represent various forms of mobile devices, such as personal digital assistants, cellular telephones, smartphones, and other computing devices. The components shown here, their connections and relationships, and their functions, are meant to be examples only, and are not meant to limit implementations of the inventions described and/or claimed in this document.

Computing device 600 includes a processor 602, memory 604, a storage device 606, a high-speed controller 608 connecting to memory 604 and high-speed expansion ports 610, and a low-speed controller 612 connecting to low-speed bus 614 and storage device 606. Each of the components 602, 604, 606, 608, 610, and 612, are interconnected using various busses, and may be mounted on a common motherboard or in other manners as appropriate. The processor 602 can process instructions for execution within the computing device 600, including instructions stored in the memory 604 or on the storage device 606 to display graphical information for a GUI on an external input/output device, such as display 616 coupled to high-speed controller 608. In other implementations, multiple processors and/or multiple buses may be used, as appropriate, along with multiple memories and types of memory. Also, multiple computing devices 600 may be connected, with each device providing portions of the necessary operations (e.g., as a server bank, a group of blade servers, or a multi-processor system).

The memory 604 stores information within the computing device 600. In one implementation, the memory 604 is a computer-readable medium. In one implementation, the memory 604 is a volatile memory unit or units. In another implementation, the memory 604 is a non-volatile memory unit or units.

The storage device 606 is capable of providing mass storage for the computing device 600. In one implementation, the storage device 606 is a computer-readable medium. In various different implementations, the storage device 606 may be a floppy disk device, a hard disk device, an optical disk device, or a tape device, a flash memory or other similar solid state memory device, or an array of devices, including devices in a storage area network or other configurations. In one implementation, a computer program product is tangibly embodied in an information carrier. The computer program product contains instructions that, when executed, perform one or more methods, such as those described above. The information carrier is a computer- or machine-readable medium, such as the memory 604, the storage device 606, or memory on processor 602.

The high-speed controller 608 manages bandwidth-intensive operations for the computing device 600, while the low-speed controller 612 manages lower bandwidth-intensive operations. Such allocation of duties is an example only. In one implementation, the high-speed controller 608 is coupled to memory 604, display 616 (e.g., through a graphics processor or accelerator), and to high-speed expansion ports 610, which may accept various expansion cards (not shown). In the implementation, low-speed controller 612 is coupled to storage device 606 and low-speed bus 614. The low-speed bus 614 (e.g., a low-speed expansion port), which may include various communication ports (e.g., USB, Bluetooth®, Ethernet, wireless Ethernet), may be coupled to one or more input/output devices, such as a keyboard, a pointing device, a scanner, or a networking device such as a switch or router, e.g., through a network adapter.

The computing device 600 may be implemented in a number of different forms, as shown in the figure. For example, it may be implemented as a standard server 620, or multiple times in a group of such servers. It may also be implemented as part of a rack server system 624. In addition, it may be implemented in a personal computer such as a laptop computer 622. Alternatively, components from computing device 600 may be combined with other components in a mobile device (not shown), such as computing device 650. Each of such devices may contain one or more of computing devices 600, 650, and an entire system may be made up of multiple computing devices 600, 650 communicating with each other.

Computing device 650 includes a processor 652, memory 664, an input/output device such as a display 654, a communication interface 666, and a transceiver 668, among other components. The computing device 650 may also be provided with a storage device, such as a micro-drive or other device, to provide additional storage. Each of the components 650, 652, 664, 654, 666, and 668, are interconnected using various buses, and several of the components may be mounted on a common motherboard or in other manners as appropriate.

The processor 652 can process instructions for execution within the computing device 650, including instructions stored in the memory 664. The processor may also include separate analog and digital processors. The processor may provide, for example, for coordination of the other components of the computing device 650, such as control of user interfaces, applications run by computing device 650, and wireless communication by computing device 650.

Processor 652 may communicate with a user through control interface 658 and display interface 656 coupled to a display 654. The display 654 may be, for example, a TFT LCD display or an OLED display, or other appropriate display technology. The display interface 656 may comprise appropriate circuitry for driving the display 654 to present graphical and other information to a user. The control interface 658 may receive commands from a user and convert them for submission to the processor 652. In addition, an external interface 662 may be provided in communication with processor 652, so as to enable near area communication of computing device 650 with other devices. External interface 662 may provide, for example, for wired communication (e.g., via a docking procedure) or for wireless communication (e.g., via Bluetooth® or other such technologies).

The memory 664 stores information within the computing device 650. In one implementation, the memory 664 is a computer-readable medium. In one implementation, the memory 664 is a volatile memory unit or units. In another implementation, the memory 664 is a non-volatile memory unit or units. Expansion memory 674 may also be provided and connected to computing device 650 through expansion interface 672, which may include, for example, a subscriber identification module (SIM) card interface. Such expansion memory 674 may provide extra storage space for computing device 650, or may also store applications or other information for computing device 650. Specifically, expansion memory 674 may include instructions to carry out or supplement the processes described above, and may include secure information also. Thus, for example, expansion memory 674 may be provide as a security module for computing device 650, and may be programmed with instructions that permit secure use of computing device 650. In addition, secure applications may be provided via the SIM cards, along with additional information, such as placing identifying information on the SIM card in a non-hackable manner.

The memory may include for example, flash memory and/or MRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 664, expansion memory 674, or memory on processor 652.

Computing device 650 may communicate wirelessly through communication interface 666, which may include digital signal processing circuitry where necessary. Communication interface 666 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through transceiver 668 (e.g., a radio-frequency transceiver). In addition, short-range communication may occur, such as using a Bluetooth®, WiFi, or other such transceiver (not shown). In addition, GPS receiver module 670 may provide additional wireless data to computing device 650, which may be used as appropriate by applications running on computing device 650.

Computing device 650 may also communicate audibly using audio codec 660, which may receive spoken information from a user and convert it to usable digital information. Audio codec 660 may likewise generate audible sound for a user, such as through a speaker, e.g., in a handset of computing device 650. Such sound may include sound from voice telephone calls, may include recorded sound (e.g., voice messages, music files, etc.) and may also include sound generated by applications operating on computing device 650.

The computing device 650 may be implemented in a number of different forms, as shown in the figure. For example, it may be implemented as a cellular telephone 680. It may also be implemented as part of a smartphone 682, personal digital assistant, or other mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. Other programming paradigms can be used, e.g., functional programming, logical programming, or other programming. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

What is claimed is:

1. A monitoring and detection system comprising:
 a wearable device compatible with and worn by an animal, the wearable device including a processing engine, one or more input/output devices, and a communication interface comprising digital signal processing circuitry configured to communicate with a remotely located base station;
 a sensor array integrated within the wearable device, the sensor array including a plurality of sensors configured to monitor an environment around the wearable device as the animal traverses a space that is proximate to a human, and generate data representing attributes of the environment and activities of the human;

a camera mounted to the wearable device, the camera being positioned for capturing images within a field of view of the animal as the animal traverses the space and observes the human; and an observation module worn by the animal;

wherein the observation module comprises a sensor for detecting motion of the animal, and one or more sensors for detecting physiological parameters of the animal.

2. The system of claim 1 wherein the one or more sensors for detecting physiological parameters of the animal further comprise one or more of a heart rate monitor for detecting a heart rate of the animal, a respiration monitor for detecting respiration of the animal, or a temperature sensor for detecting a body temperature of the animal.

3. The system of claim 2 wherein the observation module collects sensor data from the sensors and transmits the sensor data to the processing engine using wireless communication, and wherein the processing engine stores and further processes the sensor data to determine a likelihood that the animal is expressing empathy toward the human.

4. The system of claim 1 wherein the camera is one of a still camera or a video camera.

5. A monitoring and detection system comprising:
a wearable device compatible with and worn by an animal, the wearable device including a processing engine, one or more input/output devices, and a communication interface comprising digital signal processing circuitry configured to communicate with a remotely located base station;

a sensor array integrated within the wearable device, the sensor array including a plurality of sensors configured to monitor an environment around the wearable device as the animal traverses a space that is proximate to a human, and generate data representing attributes of the environment and activities of the human;

a camera mounted to the wearable device, the camera being positioned for capturing images within a field of view of the animal as the animal traverses the space and observes the human;

a motion sensor configured to detect movements of the animal toward the human; and a processor configured to analyze the detected movements of the animal, including determining how the animal is moving as a behavioral response to the human, to determine a likelihood that the animal is expressing empathy toward the human, and report the determined likelihood.

6. The system of claim 5 comprising a microphone configured to monitor sounds made by the animal, wherein the processor is configured to analyze the sounds made by the animal, during a time when the animal is observing or interacting with the human, in combination with the detected movements of the animal to determine the likelihood that the animal is expressing empathy toward the human.

7. The system of claim 6 comprising a GPS device configured to generate GPS data to track movements of the animal, wherein the processor is configured to analyze the tracked movements of the animal in combination with the detected movements of the animal and the sounds made by the animal to determine the likelihood that the animal is expressing empathy toward the human.

8. The system of claim 7 wherein the microphone and the GPS device are included in the sensor array, and the sensor array further includes a temperature sensor and a smoke and carbon monoxide detector.

9. The system of claim 6 comprising:
a heart rate monitor configured to sense a heart rate of the animal; and a respiration monitor configured to detect respiration of the animal;

wherein the processor is configured to analyze the heart rate of the animal, and the detected respiration of the animal, in combination with the detected movements of the animal and the sounds made by the animal to determine the likelihood that the animal is expressing empathy toward the human.

10. The system of claim 9 comprising an observation module worn by the animal, wherein the motion sensor, the heart rate monitor and the respiration monitor are included in the observation module, and the observation module further includes a body temperature sensor.

11. The system of claim 6 wherein the processing engine comprises the processor and a memory and data storage.

12. A monitoring and detection system comprising:
a wearable device compatible with and worn by an animal, the wearable device including a processing engine, one or more input/output devices, and a communication interface comprising digital signal processing circuitry configured to communicate with a remotely located base station;

a sensor array integrated within the wearable device, the sensor array including a plurality of sensors configured to monitor an environment around the wearable device as the animal traverses a space that is proximate to a human, and generate data representing attributes of the environment and activities of the human;

a camera mounted to the wearable device, the camera being positioned for capturing images within a field of view of the animal as the animal traverses the space and observes the human; and a processor configured to analyze the data generated by the sensor array to determine a current location of the human and activities of the human over a period of time, and report on the current location of the human and the activities of the human over the period of time.

13. The system of claim 12 wherein the processor is configured to evaluate the activities of the human over the period of time to detect whether the human is in danger.

14. The system of claim 12 wherein the processor is configured to evaluate the activities of the human over the period of time to detect whether the human is following prescribed procedures.

15. The system of claim 12 wherein the processor is configured to compare the activities of the human over the period of time with historical activity information of the human to determine an activity level of the human.

16. The system of claim 15 wherein the processor is configured to determine whether the activity level of the human exceeds a predetermined minimum activity level for the human.

* * * * *